(12) United States Patent
Kaplan (10) Patent No.: US 7,189,245 B2
(45) Date of Patent: Mar. 13, 2007

(54) SUBRETINAL IMPLANTATION DEVICE AND SURGICAL CANNULAS FOR USE THEREWITH

(75) Inventor: Henry J. Kaplan, Louisville, KY (US)

(73) Assignee: Photogenesis, Inc., Los Angeles, CA (US)

( * ) Notice: Subject to any disclaimer, the term of this patent is extended or adjusted under 35 U.S.C. 154(b) by 615 days.

(21) Appl. No.: 10/367,353

(22) Filed: Feb. 14, 2003

(65) Prior Publication Data

US 2003/0216747 A1 Nov. 20, 2003

Related U.S. Application Data

(60) Provisional application No. 60/357,410, filed on Feb. 14, 2002.

(51) Int. Cl.
*A61F 9/00* (2006.01)
(52) U.S. Cl. .................................................. 606/107
(58) Field of Classification Search ............ 606/107, 606/108; 623/6.11, 6.12, 6.13, 5.15, 5.16
See application file for complete search history.

(56) References Cited

U.S. PATENT DOCUMENTS

| | | |
|---|---|---|
| 3,934,591 A | 1/1976 | Gleason |
| 4,014,342 A | 3/1977 | Staub et al. |
| 4,304,866 A | 12/1981 | Green et al. |
| 4,418,691 A | 12/1983 | Yannas et al. |
| 4,495,288 A | 1/1985 | Jarvis, Jr. et al. |
| 4,563,779 A | 1/1986 | Kelman |
| 4,655,774 A | 4/1987 | Choyce |
| 4,662,869 A | 5/1987 | Wright |
| 4,693,686 A | 9/1987 | Sendax |
| 4,702,697 A | 10/1987 | Linkow |
| 4,727,018 A | 2/1988 | Eichner et al. |

(Continued)

FOREIGN PATENT DOCUMENTS

DE    40 04 921    8/1991

(Continued)

OTHER PUBLICATIONS

Anderson; "Retinal Detachment in the Cat; The Pigment Epithelial-Photoreceptor Interface", Invest. Opthalmol. Vis. Schi., vol. 24, pp. 906-926, Jul. 1983.

(Continued)

*Primary Examiner*—Kevin T. Truong
(74) *Attorney, Agent, or Firm*—Daniel B. Schein, Esq.

(57) ABSTRACT

An implantation device having a reservoir for holding a solid or semisolid implant and a carrier fluid, wherein the reservoir includes a cannula. The cannula has a tip end and a delivery opening therein both shaped and dimensioned to suit the application. For example, an implant (such as a retinal cell graft) and suitable carrier fluid (such as an aqueous hyaluronic acid solution) can be expressed from the opening into the subretinal space of a recipient eye, provided the cannula is of sufficient length that the tip end can reach the subretinal space while the remainder of the fluid reservoir is external of the eye. Expression of the carrier fluid from the reservoir via the delivery opening expels the implant through the delivery opening. An electromechanically driven plunger apparatus with operator controls is provided in a preferred embodiment.

20 Claims, 10 Drawing Sheets

U.S. PATENT DOCUMENTS

| | | | |
|---|---|---|---|
| 4,868,116 A | | 9/1989 | Morgan et al. |
| 4,900,300 A | | 2/1990 | Lee |
| 4,919,130 A | * | 4/1990 | Stoy et al. ............... 606/107 |
| 4,927,676 A | | 5/1990 | Williams |
| 4,940,468 A | | 7/1990 | Petillo |
| 4,963,489 A | | 10/1990 | Naughton et al. |
| 5,000,963 A | | 3/1991 | Hefton |
| 5,292,802 A | | 3/1994 | Rhee et al. |
| 5,300,029 A | | 4/1994 | Denance |
| 5,308,889 A | | 5/1994 | Rhee et al. |
| 5,316,452 A | | 5/1994 | Bogen et al. |
| 5,322,691 A | | 6/1994 | Darougar et al. |
| 5,323,788 A | | 6/1994 | Silvestrini et al. |
| 5,324,260 A | | 6/1994 | O'Neill et al. |
| 5,326,346 A | | 7/1994 | Cortes |
| 5,326,584 A | | 7/1994 | Kamel |
| 5,328,481 A | | 7/1994 | Wang |
| 5,342,370 A | | 8/1994 | Simon et al. |
| 5,374,515 A | | 12/1994 | Parenteau et al. |
| 5,533,981 A | | 7/1996 | Mandro et al. |
| 5,702,441 A | * | 12/1997 | Zhou ..................... 623/6.11 |
| 5,720,742 A | | 2/1998 | Zacharias |
| 5,817,075 A | | 10/1998 | Giungo |
| 5,868,728 A | | 2/1999 | Giungo et al. |
| 5,941,250 A | | 8/1999 | Aramant et al. |
| 5,962,027 A | | 10/1999 | Hughes |
| 6,045,791 A | | 4/2000 | Liu |
| 6,156,042 A | | 12/2000 | Aramant |
| 6,159,218 A | | 12/2000 | Aramant et al. |
| 6,273,894 B1 | * | 8/2001 | Dykes ..................... 606/107 |
| 6,514,238 B1 | | 2/2003 | Hughes |

FOREIGN PATENT DOCUMENTS

| | | |
|---|---|---|
| EP | 0 340 698 | 11/1989 |
| EP | 0 535 506 | 4/1993 |

OTHER PUBLICATIONS

Aramant; "The Fate of Retinal Ganglion Cells, Retrogradely Labeled with Fluorogold and Transplanted to Rate Retina", Suppl. Invest. Ophthalmol. Vis. Sci., 32:983, abs. #1545, 1991.

Axen; "Chemical Coupling of Peptides and Proteins to Polysaccharides by Means of Cyanogen Halides", nature, 214:1302-1304, Jun. 24, 1967.

Bignami; "The Radial Glial of Muller in the Rat Retina and Their Response to Injury. An Immunofluorescene Study with Antibodies to the Glial Fibrillary Acidic (GFA) Protein", Exp. Eye Res., 28:63-69, (1979).

Bjorklund; "Neural Grafting in the Mammalian CNS", Elsevier Science Publishing B.V., Netherlands, Ch. 38, pp. 431-436, 1985.

Bonds; "Visually evoked potentials and deoxyglucose studies of monocularly deprived cats", Suppl. Invest. Opthalmol. Visual Sci. 18:225, abs. #11, Apr. 1980.

Cuatrecasas; "Selective Enzyme Purification by Affinity Chromatography", Biochemistry Cuatrecasas et al., 61:636-643, Aug. 9, 1968.

del Cerro; "Intraocular Retinal Transplants", Invest. Ophthalmol, Vis. Sci., vol. 26, pp. 1182-1185, Aug. 1985.

del Cerro; "Intraretinal transplatation of fluorescently labeled retinal cell suspensions", Neurosci. Lt., 92 pp. 21-26, (1988).

del Cerro; "Retinal Transplants", Progress in Retinal Research, vol. 9, chapter 6, pp. 229-269, 1990.

Del Priore, "Experimental and surgical aspects of retinal pigment epithelial cell transplantation", Eur. J. Implant Ref. Surg. 5:128-131, Jun. 1993.

Del Priore, "Differential ability of aged versus young human Bruch's Membrane to support repopulation by health RPE", Invest. Ophthalmol. Vis. Sci. 34:834, #4, abs #652, Mar. 15, 1993.

Faktorovich, "Photoreceptor Degeneration in Inherited Retinal Dystrophy Delayed by Basic Fibrolast Growth Factor", Nature, 347:83-86, Sep. 6, 1990.

Faktorovich, "Basic Fibroblast Growth Factor and Local Injury Protect Photoreceptors for Light Damage in the Rat", vol. 12(9) Journal of Neuorscience pp. 3554-3567, Sep. 1992.

Fang, "Development of a surgical procedure and instrument for transplantation of extended gelatin sheets to the subretinal space", Invest. Ophthalmol. Vis. Sci. 34:1096, #4, abs. #1981-1974, Mar. 15, 1993.

Gao, "Low immunogenicity of neonatal murine photoreceptor cells for cytotoxic lymphocytes in mice", Invest. Ophthalmol. Vis. Sci. 33:1285, #4, abs #2963, Mar. 15, 1992.

Gouras, "Reconstruction of Degenerate rd Mouse Retina by Transplantation of Transgenic Photoreceptors", Invest. Ophthal. & Vis. Sci., vol. 33/9, pp. 2579-2586, Aug. 1992.

Hicks "Different Rhodopsin Monoclonal Antibodies Reveal Different Binding patterns on Developing and Adult Rat Retina", Jour. on Histochemistry & Cytochemistry, vol. 35, No. 11, pp. 1317-1328, (1987).

Honig, "Fluorescent Carbocyanine Dyes Allow Living Neurons of Identified Origin to be Studied in Long-term Cultures", Jour. of Cell Biology, 103:171-187, Jul. 1986.

Hughes, "Transplantation of Retinal Photoreceptors to Dystrophic Retina", Society Sci. Abstr. 1277, abs. #511-16, Nov. 1988.

Hughes, "Transplanted Photoreceptors Form Synapses in Light-Damaged Retina", Suppl. Invest. Ophthalmol. Vis. Sci., 31:594, abs. #2908-6, 1990.

Hughes, "Differential survival of sensory elements in intracranial otic transplants", Soc. Neurosci., 17:1138, abs. #452.12, Nov. 10-15, 1991.

Hughes, "Quantification of synapses in light-damaged retina reconstructed by transplantation of photoreceptors", Invest. Ophthalmol. Vis. Sci., #4, 33:1058, abs. 1832-3, Mar. 15, 1992.

Hughes, "Explorations of optic transplantations", Experimental Neurology, 115:37-43, 1992.

Kaplan, "Retinal pigment epithelium regeneration in the non-human primate", Suppl. Invest. Ophthalmol. Vis. Sci. #4, abs. #2173, Mar. 15, 1992.

Kitchell, "Poly(lactic/glycolic acid) biodegradable Drug-Polymer Matrix Systems", Methods in Enzymology, 112:436-448, Chapter 32, (1985).

Klassen, "Retinal transplants can drive a pupillary reflex in host rat brains", Proc. Natl. Acad. Sci. U.S.A., vol. 84, pp. 6958-6960, Oct. 1987.

Klassen, "Anatomincla and Behavioral correlates of a Xenograft-Mediated Pupillary Reflex", Experimental Neurology 102, 102-108, (1988).

Lane, Transplantation of Retinal Pigment Epithelium Using a Pars Plana Approach, Eye, 3:27-32, 1989.

LaVail, "Histotypic Organization of the Rat Retina in Vitro", Z. Zellforsch, Springer Verlag, 114:557-579, 1971.

LaVail, "Multiple Growth factors, Cytokines, and Neurotrophins Rescue Photoreceptors from the Damaging Effects of Constant Light", Neurobiology, vol. 89, pp. 11249-11253, Dec. 1992.

Li, "Transplantation of Retinal Pigment Epithelial Cells to Immature and Adult Rat Hosts: Short- and Long-term Survival Characteristic", Exp. Eye Res. 47:771-785 (1988).

Li, "Inherited Retinal dystrophy in the RCS Rat: Prevention of Photoreceptor Degeneration by Pigment Epithelial Cell Transplantation", Exp. Eye Res. 47:911-917, (1988).

Li, "Optimal Coditions for Long-term Photoreceptor Cell Rescue in RCS Rats: The Necessity for Healthy RPE Transplants", Exp. Eye Res. 52:669-679, (1991).

Liu, "Photoreceptor inner and outer segments in transplanted retina", Soc. Neurosci., 16:405, abs. #171.1, 1990.

Liu, "Transplantation of confluent sheets of adult human RPE", Invest. Ophthalmol. Vis. Sci. 33:1128, #4, abs. #2180, Mar. 15, 1992.

Liu, "Transplantation of confluent sheets of adult human and rat RPE on a thin substrate", Suppl. Invest. Ophthalmol. Vis. 34:1112, abs. #2018-50, 1993.

Lopez, "Transplanted retinal Pigment Epithelium Modifies the Retinal Degeneration in the RCS Rat", Invest. Ophthalmol. & Vis. Sci., 30:586-589, #3, Mar. 1989.

MacLeish, "Growth and Synapse Formation Among Major Classes of Adult Salamander Retinal Neurons in Vitro", Neuron, vol. 1, pp. 751-760, Oct. 1988.

Mayerson, "An Improved Method for Isolation and Culture of Rat Retinal Pigment Epithelial Cells", Invest. Ophthalmol. & Vis. Sci., 26:1599-1609, Nov. 1985.

McConnell, "Regeneration of ganglion cell axons in the adult mouse retina", Brain Research, 241:362-365 (1982).

Maurice, "Keratoplasty with Cultured Endothelium on Thin Membranes", Arvo Abstracts, Supp. Inv. Ophthalmol. and Vis. Sci., pp. 10, abs #9, Apr. 1979.

McCulley, "Corneal Endothelial Transplantation", Ophthalmol., vol. 87 , #3, pp. 194-201, Mar. 1980.

McCulley, "A Gelatin Membrane Substrate for the Transplantation of Tissue Cultured Cells, Transplantation", vol. 29, No. 6, pp. 498-499, Jun. 1980.

Mollenhauer, "Plastic Embedding Mixtures for use in Electron Microscopy", Stain Tech., 39:111-114.

Moritera, Transplants of monolayer retinal pigment epithelium grown on biodegradable membrane in rabbits, Invest. Ophthalmol. Vis. 34: #4, abs. 1919-75, Mar. 15, 1993.

Muller, "Morphology and synaptic inputs to lucifer yellow injected bipolar cells in rat retinal slices", Soc. Neurosci., 17:1013, abs. #403.4, Nov. 10-15, 1991.

Muller, "Rod and cone inputs to bipolar cells in the rat retina", Inves. Ophthalmol. Vis. Sci. 34:984, #4, abs. #1387, Mar. 15, 1993.

Mueller, "Autotransplantation of Retinal Pigment Epithelium in Intravitreal Diffusion Chamber", vol. 80, No. 3, Part II Retinal Pigment Epithelium, p. 530-537, 1993.

Newsome, "Transplantation of Human Retinal Pigment Epithelium Into Primate Model of Mascular Degeneration", Retina Society Meeting, Toronto, Canada, Sep. 1991.

O'Steen, Retinal and Optic Nerve Serotonin and Retinal Degeneration as Influenced by Photoperiod, Exp. Neurology, 27:194-205, 1970.

Pfeffer, Improved Methodology for Cell Culture of Human and Monkey Retinal Pigment Epithelium, Chapter 10, Progress in retinal research, vol. 10, pp. 251-291, 1991.

Politi, Generation of Enriched Populations of Cultured Photoreceptor Cells, Invest. Ophthalmol. Vis. Sci., vol. 27, No. 5, pp. 656-665, May, 1986.

Powell, "Controlled release of nerve growth factor from a polymeric implant", Brain Res., 515:309-311, 1990.

Pu, "Biochmical Interruption of Membrane Phospholipid Renewal in retinal Photoreceptor Cells", Jour. of Neurosci., vol. 4, No. 6, pp. 1559-1576, Jun. 1984.

Radtke, "Pharmacological Therapy for Proliferative Vitreoretinopathy", vol. 224 Graefe's Archive Ophthalmol. pp. 230-233, 1986.

Royo, "Retinal Transplantation from Fetal to Maternal Mammalian Eye", Growth, 23:313-336, 1959.

Sarthy, Isolated Cells from a Mammalian Retina, Brain Research, 176:208-212, 1979.

Schuschereba, "Retinal cell and photoreceptor transplantation between adult New Zealand Red Rabbit Retinas", Experimental Neurology. 115:95-99, 1992.

Sheedio, Functional and Structural Characteristics of Photoreceptor Cells Rescued in RPE-cell Grafted Retinas of RCS Dystrophic Rats, 48:841-854, 1989.

Shiosaka, "A simple method for the separation of retinal sublayers from the entire retina with special referecne to application for cell culture", Jour. Neurosci. Methods, 10:229-235, 1984.

Silverman, "Deoxyglucose mapping of Orientation and spatial frequency in cat visual cortex", Suppl., Invest. Ophthalmol. Visual Sci. 18:225, abs #10, 1980.

Silverman, "Deoxyglucose mapping of orientation in cat visual cortix", Recent Advances in Vision. Optical Society of America Technical Digest. SA13, 1980.

Silverman, "The retinotopic organization of cat striate cortex", Suppl. Invest Ophthalmol. Visual Sci. 22:105, abs. #1, 1982.

Silverman, "Department of Health and Human Services Grant Application, Transplantation of Mammalian Photoreceptors", Martin S. Silverman, pp. 1-13, submitted May, 1986, funded by NEI Sep. 11, 1986, Grant No. 1RO3 EY 06943-01.

Silverman, "Department of Health and Human Services Grant Application, Transplantation of Mammalian Photoreceptors", Martin S. Silverman, pp. 1-61, submitted May, 1987, funded by NEI Feb. 16, 1988, Grant No. IRO1 EY07547-01.

Silverman, Transplantation of retinal photoreceptors to light damaged retina, Suppl., Invest. Ophthalmol. Vis. Sci. 28:288, abs #11, 1987.

Silverman, Transplantation of retinal photoreceptors to light damage retina: Survival and integration of receptors from a range of postnatal ages, Soc. Neurosci. Abstr. 17:1301, abs. #360.17, 1987.

Silverman, Transplantation of Human Photoreceptors to Light Damaged Retina, Soc. Neurosci. Abstr. 18:1278, abs. #511.17, 1988.

Silverman, "Photoreceptor transplantation in inherited and environmentally induced retinal degeneration: Anatomy, Immunohistochemistry and Function. Inherited and Environmentally Induced Retinal Degeneration", (ed., MM LaVail, RE Anderson, and JG Hollyfield) Alan r. Liss publisher, pp. 687-704., 1989.

Silverman, "Photoreceptor rescue in the RCS rat without pigment epithelium transplantation", Soc. Neurosci., 15:115, abs #51.1, Oct. 19-Nov. 3, 1989.

Silverman, "Transplantation of Photoreceptors to Light Damaged Retina", Invest. Ophthalmol. Vis. Sci., vol. 30, No. 8, 1684-1690, Aug. 1989.

Silverman, Light Dependent Activation of Light Damaged Retina by Transplanted Photoreceptors, Suppl., Invest. Ophthalmol. Visual Sci., 30:208, abs. #9, 1989.

Silverman, "Transplantation of Human and Non-Human Primate Photoreceptors to Damaged Primate Retina", Invest. Ophthalmol. Visual Sci., 31:594, abs #2909-7, 1990.

Silverman, "Photoreceptor rescue in the RCS rat without pigment epithelium transplantation", Curr. Eye Res. 9:183-192, #2, 1990.

Silverman, "Photoreceptor transplantation to dystrophic retina. Retinal Degeneration", (ed. Anderson R.E., LaVail, MM, and Hollyfield J.G.). CRC Press, Inc., Boca Raton, Florida, pp. 321-335, Chapter 29, 1991.

Silverman, "Restoration of the pupillary reflex by photorecelptor transplantation", Suppl., Invest. Ophthalmol. Vis. Sci. 32:983, abs #1548, 1991.

Silverman, "Photoreceptor transplantation: Anatomic, electrophysiologic and behavioral evidence for the functional reconstructuon of retinas lacking photoreceptors". Soc. Neurosci.17:12, abs. #9.4, Nov. 10-15, 1991.

Silverman, "Photoreceptor transplantation: Anatomic, electrophysiologic and behavioral evidence for the functional reconstruction of retinas lacking photoreceptors", Experimental Neurology 115:87-94, 1992.

Silverman, "Rescue of host ones by transplanted donor photoreceptors in the rd mouse", Invest. Ophthalmol. Vis. Sci. 34:1096, #4, abs. #1937-93, Mar. 15, 1993.

Silverman, Transplantation of Retinal Photoreceptors to Light-Damaged Retina, 288 Arvo Abstracts, abs. #11.

Simmons, "Physiological Responses in Retinal Transplants and Host Tecta Evoked by Electrical or Photic Stimulation of Transplanted Embryonic Retinae", Soc. Neurosci. Abstr. 10:668, abs #196.5.

Sokoloff, "the [C]Deoxyglucosel Method for the Measurement of Local Cerebral Glucose Utilization: Therory, Procedure, and Normal Values in the Conscious and Anesthetized Albino Rat", Jour. of Neurochem., 28:897-916, 1977.

Solomons, Special Topic M Photochemistry of Vision Organic Chemistry, 5th Ed., Univ. of FL, Pub. Wiley & Sons, pp. 1168-1171, 1991.

Tootell, "Deoxyglucose mapping of color and spatial frequency organization in monkey and Cat Cortex", Recent Advances in Vision. Optical Society of America Techn. Digest. SA14, 1980.

Tootell, "Color-Dependent Deoxyglucose Patterns Within Macaque Cortex", Arvo Abstracts 226, Suppl., Invest. Ophthalmol. Vis. Sci. pp. 226, abs. #12, Apr. 1980.

Tootell, "2DG study of retinotopic organization in macaque striate cortex", Suppl., Invest. Ophthalmol. Visual Sci. 22:12, #3, abs. #14, Mar. 1982.

Tootell, "Deoxyglucose analysis of retinotopic organization in primate striate cortex", Sci. 218:902-904, Nov. 26, 1982.

Tootell, "Two methods for flat-mounting cortical tissue", Journal Neursci. Methods, 15:177-190, 1985.

Townes, "Rod Photoreceptors Dissociatd from the Adult Rabbit Retina", Jour. of Neuroscience, vol. 8, No. 1, pp. 320-331, Jan., 1988.

Turner, "Newborn Rat Retinal Cells Transplanted Into a Retinal Lesion Site in Adult Host Eyes", Develop. Brain Research, 26:91-104, (1986).

Valentino, Transplanted photoreceptors form synapses in reconstructed RCS rat retina. Soc. Neurosci., 16:405, abs #171.2, Oct. 28-Nov. 2, 1990.

Valentino, "Photoreceptor rescue in RCS rat and rd mouse by heat shock", Suppl., Invest. Ophthalmol. Vis. Sci., 31:594, abs. #2911-9, 1990.

Valentino, "Photoreceptor sheets isolated from the neonatal rat retina lack synapses and other retinal cells", Soc. Neuroscience. 18:838, abs. #352-8, Oct. 25-30, 1992.

Weiss, Transplanting the Light Fantastic Cells from eye donors may someday restore vision in some blind individuals, Science News, vol. 136, No. 19, pp. 297-300, Nov. 4, 1989.

Wilcheck, "Immobilization of Enzymes and Affinity Ligands onto Agarose Via Stable and Uncharged Carbamate Linkages", Biochem. In'l. vol. 4, No. 6, pp. 629-635, Jun. 1982.

Wise, Lactic/Glycolic Acid Polymer, Drug Carriers in Biology and Medicine (ed. Gregoriaris) 1979 Chapter 12, pp. 237-270.

Zucker, "Synaptic Microcircuitry of Rat Retinal Transplants Ultrastructural Observations", Suppl., Invest. Ophthalmol. Vis. Sci., 31:594, abs. #2906-4, 1990.

\* cited by examiner

SUBRETINAL IMPLANTATION DEVICE AND SURGICAL CANNULAS FOR USE THEREWITH

PRIORITY INFORMATION

This application claims priority of U.S. provisional patent application Ser. No. 60/357,410, filed Feb. 14, 2002, which application is specifically incorporated by reference as reproduced in full below.

FIELD OF THE INVENTION

The present invention relates in general to surgical instruments and surgical techniques. More particularly, the present invention in one aspect is directed to a surgical tool for transplanting tissues, such as retinal cells, epithelial tissue and/or choroidal tissue through an incision in the eye. The present invention is also directed to devices and methods for implanting solids, semisolids, and fluids into a mammalian body, and for implantation of same into mammalian eyes, preferably human eyes. The present invention in another aspect is directed to devices and methods for implanting solids, semisolids, and fluids into the subretinal space of a mammalian eye, preferably where the mammalian eye is a human eye.

BACKGROUND OF THE INVENTION

Since the surprising discovery in the late 1980's that retinal cells can be safely transplanted into the subretinal space of mammals, and that this could have potential benefit, and the pioneering work by the present inventor and colleagues beginning in mid-1990's that such transplants could also be safely delivered into humans, there has been an ever-increasing interest in devices and methods for implanting materials into the back of the eye. Recent, widely publicized human studies involving implantation of phototransducing devices into patients having retinal diseases have added further to the demand for and interest in devices and methodologies for implanting materials into the eye, and in particular devices and methodologies for epiretinal and subretinal implantation. Subretinal implantation refers to implanting materials beneath the retina, for example between the retina and the choroid or between the retina and the retinal pigment epithelium (RPE). Epiretinal implantation refers to implanting materials into the eye on top of the retina or close thereto, and also includes attachment thereof to the upper surface of the retina.

There are a variety of references know to those skill in the art that address ophthalmic pathologies. There are very limited, currently available treatments for retinal pathologies. However, one of ordinary skill in the art will be familiar with publications disclosing methods and apparatuses for conducting related research, and methods, instruments, and implantable materials and devices for treatment and/or proposed treatment of ophthalmic diseases and injuries. Specifically incorporated by reference as if reproduced in full below are U.S. Pat. No. 6,514,238, entitled Method For Preparation And Transplantation Of Volute Grafts And Surgical Instrument Therefor, U.S. Pat. No. 6,045,791, entitled Retinal Pigment Epithelium Transplantation, U.S. Pat. No. 6,036,678, entitled Method For Preparation And Transplantation Of Planar Implants And Surgical Instrument Therefor, U.S. Pat. No. 5,962,027, Retinal Cell Transplant, U.S. Pat. No. 5,868,728, entitled Medical Linear Actuator For Surgical Delivery, Manipulation, And Extraction, U.S. Pat. No. 5,817,075, entitled Method for preparation and transplantation of planar implants and surgical instrument therefore, Vaughan, Daniel, et al., General Ophthalmology, Appleton & Lange (1999), and Kaplan et al., "Human Photoreceptor Transplantation in Retinitis Pigmentosa, A Safety Study," *Archives of Ophthalmology*, 115:1168–1171 (1997).

The foregoing patents disclose inter alia devices for ophthalmic implantation of solid and semisolid implants. In particular, devices are disclosed that utilize a plunger-in-tube arrangement, wherein the plunger may extend substantially to or beyond an opening in the tip of a cannula inserted into an eye to express material contained therein by (1) direct physical contact between the plunger distal end and the implant, or (2) via direct physical contact between a solid or semisolid bumper driven by direct physical contact with the plunger distal end. Such "direct drive" devices are desirable due to the high level of control over the implant delivery speed, with minimal deviations due to temperature variations or hysteresis. Also disclosed is the desirability of using a fluid or hydraulic "bumper" between the distal end of the plunger and the implant, but a means for accomplishing this was not disclosed.

Use of a solid plunger has been found in some instances to lead to damage to the implant. In some instances, the implant composition sticks to the interior of the delivery cannula, making it desirable to surround the implant with a lubricant or carrier solution. However, an implantation device did not exist wherein the implant could be readily loaded into the device with an appropriate carrier or lubricant solution, and delivered with a high degree of control, such as the high degree of control needed for subretinal implantation. Excessive flow or pressure could detach or damage the retinal or other eye structures, whereas insufficient pressure or flow will not express the implant. Excessive size of the delivery opening could lead to leakage of carrier fluid and a loss of control, but insufficient size of the delivery opening can cause an excessive focused fluid flow pressure, prevent expression of the implant, or damage the implant upon expression.

Thus, there remains a need for an implantation device, particularly an implantation device for use in ophthalmic implantation, wherein the implant can be delivered in a fluid carrier, as well as methods for fabrication, loading, and use thereof.

SUMMARY OF THE INVENTION

The present invention is directed to an implantation device for implanting a solid or semisolid implant into a mammal or human. The device has a reservoir for holding an implant and a carrier fluid, wherein the reservoir includes a cannula. The cannula has a tip end and a delivery opening therein both shaped and dimensioned to suit the application. For example, an implant (such as but not limited to a retinal cell graft) and suitable carrier fluid (such as but not limited to an aqueous hyaluronic acid solution) can be expressed from the opening into the subretinal space of a recipient eye, provided the cannula is of sufficient length so that the tip end can reach the subretinal space while the remainder of the fluid reservoir is external of the eye. Expression of the carrier fluid from the reservoir via the delivery opening expels the implant through the delivery opening. An electromechanically driven plunger apparatus with operator controls is provided in a preferred embodiment.

In an embodiment, the reservoir further comprises a plunger opening and a plunger travel channel, wherein a plunger may be inserted through the plunger opening into the plunger travel channel to express fluid in the reservoir.

The device preferably further comprises a plunger at least partially slidably disposed in the plunger travel channel. The reservoir preferably further comprises a loading channel and a loading channel opening, wherein the loading channel may be accessed via the loading channel opening independently of the plunger opening.

The loading channel is operatively connected to the plunger travel channel at a junction point. The plunger may slidably travel through the plunger travel channel towards the cannula sufficiently past said junction point to block fluid flow into the loading channel caused by further plunger travel.

A handpiece is operatively connectable to the reservoir (the reservoir may also referred to as a delivery cannula or tip), wherein the handpiece comprises an electromechanical drive apparatus, and the plunger is drivable thereby. The drive apparatus further comprises operator controls for controlling forward and reverse motion of the plunger in the plunger travel channel. A control unit can be remotely connected to the drive apparatus, wherein the control unit comprises operator controls and a power supply for the drive apparatus. Preferably the operator controls comprise a footpedal for at least in part operating the control unit.

In a preferred embodiment, a retinal cell graft can be loaded into the reservoir, preferably mixed with a suitable carrier fluid.

The plunger is preferably connectable and disconnectable to the electromechanical drive apparatus by a user at the site of use, so that it can be sterilized independent of the handpiece.

Also disclosed is a method for subretinal or epiretinal implantation of a solid or semisolid implant into a mammal or human eye, comprising the steps of combining a carrier fluid with a solid or semisolid implant in a reservoir, wherein the reservoir includes a cannula, the cannula having a tip end and a delivery opening therein both shaped and dimensioned to permit the delivery opening to reach sufficiently to be epiretinally located or to reach into the subretinal space of a mammalian or human eye for the desired purpose while the remainder of the fluid reservoir is external of the eye, inserting the tip end of the cannula sufficiently into a mammalian or human eye that the delivery opening is located at the desired epiretinal or subretinal location while a portion of the reservoir is external of the eye, and expressing the carrier fluid through the delivery opening sufficient to express the implant from the delivery opening into the desired location.

Preferably, the method and device of the present invention are used to implant a retinal cell graft, wherein the expression step comprises expressing the graft beneath the retina of the eye.

The present invention in another aspect discloses a system for implanting solid or semisolid implants into a mammal or human, comprising a plunger, an electromechanical drive mechanism, wherein the drive mechanism is operatively connectable to the plunger, a control mechanism and operator controls, the operator controls permitting an operator to operate the drive mechanism to control the speed and direction of movement of the plunger, the plunger being dimensioned and the drive mechanism being capable of driving the plunger at travel speeds sufficient to express fluid from a reservoir containing fluid and a semisolid or solid implant into a desired location in a mammal or human wherein the implant is expressed in the desired location. The system may include combinations of the features described above, and may also be useful for controlled infusion and aspiration.

The present invention will be better understood with reference to the description of exemplary embodiments, facilitated by reference to the following figures.

DETAILED DESCRIPTION OF PREFERRED EMBODIMENTS

Figure 1:
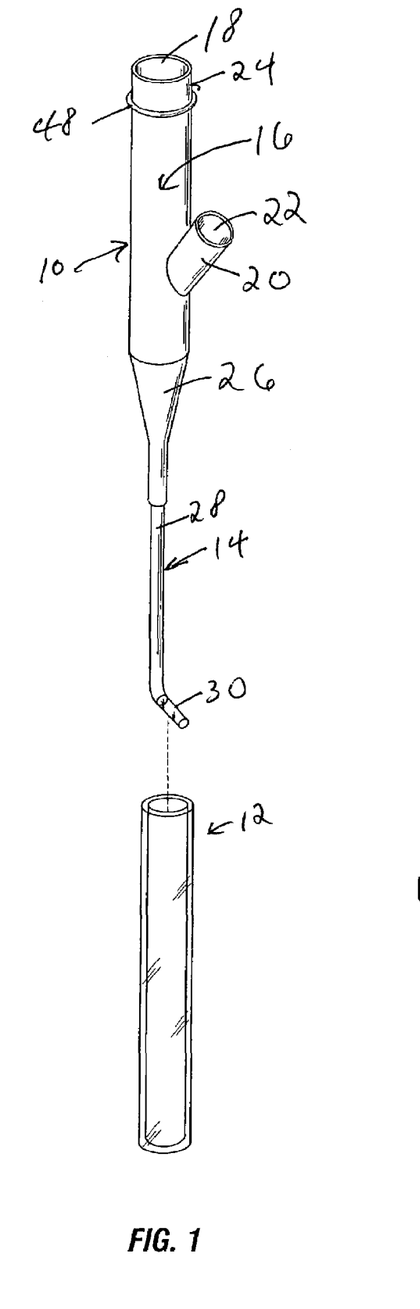
FIG. 1 illustrates a side elevation view of an exemplary reservoir of the present invention, in combination with a protective sleeve for the cannula portion thereof.

With reference to FIG. 1, a side elevation view of an exemplary reservoir 10 of the present invention is illustrated, in combination with a protective sleeve 12 for the cannula portion 14 thereof. The reservoir or tip is designed to be disposable and readily attachable and detachable from a handpiece, such as those in FIGS. 1 and 2. The reservoir 10 includes a plunger travel channel 16 inside of the main body which has a plunger opening to permit a plunger to be slidably inserted into channel 16, as a standard syringe.

An optional loading channel 20 is accessible via a loading channel opening 22, and permits fluids and implants to be placed into reservoir 10, even when it is attached to a handpiece at plunger end 24. Preferably, the plunger travel channel terminates in a funnel shaped portion 26 which guides a semisolid or solid implant into a smaller diameter implantable cannula 28, which can be of a relatively rigid material, such a hard surgical grade plastic or stainless steel to facilitate implantation and manipulation in the body of a mammal or human. Preferably, the length of cannula 28 is sufficient to at least extend from outside of an eye to the subretinal space of the eye. A clear tip 30 is preferably provided at the distal end of cannula 28. Tip 30 can be made of a soft material such as Teflon® tubing, or other clear plastic such as polycarbonate. A clear material enables the user to visually monitor the expression of an implant from the tip. The bend at the distal end of the cannula 28, can be eliminated in some instances. The tip 30 can be bent to accommodate the shape of the back of the eye or for the desired use.

Figure 2:
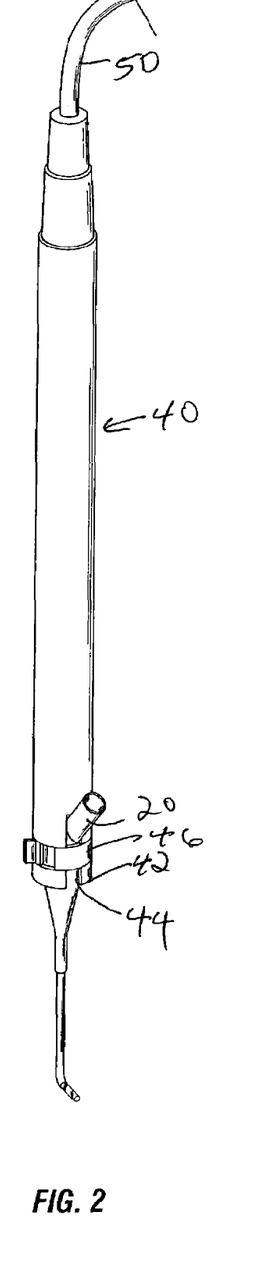
FIG. 2 illustrates an exemplary handpiece of the present invention containing an electromechanical drive mechanism and being detachably connected to a reservoir of the present invention, wherein the handpiece is connected to a remote power and control unit via a suitable cable.
Figure 3:
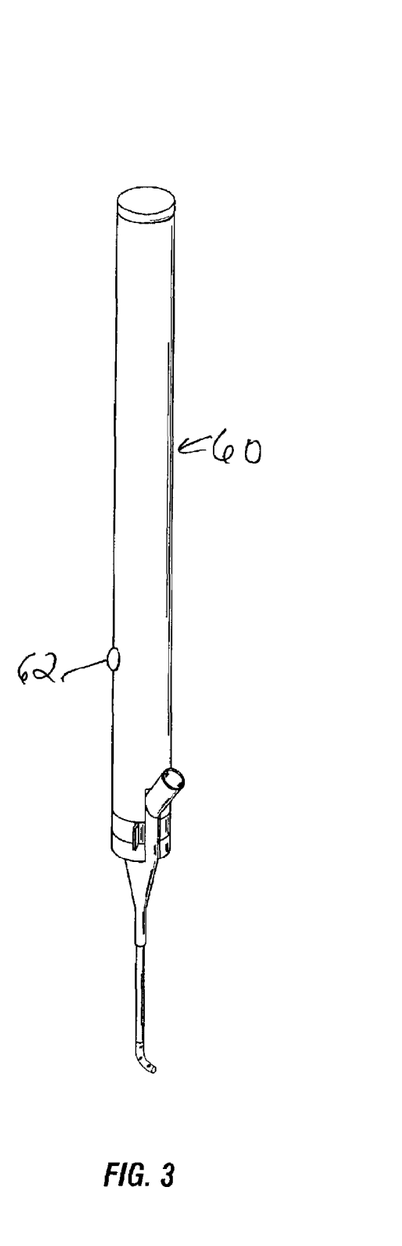
FIG. 3 illustrates an exemplary battery operated handpiece of the present invention, which also contains operator controls and an electromechanical drive mechanism.

With reference to FIG. 2, an exemplary handpiece 40 of the present invention is illustrated. Handpiece 40 has a distal end 42 having an opening to receive a reservoir. An optional slot 44 is provided to accommodate loading channels on reservoirs. A reservoir can be retained in the distal end 42 by a sliding annular band 46 that partially encircles the circumference of a corresponding detent in the handpiece outer housing. In the event that the reservoir does not have a loading channel, an annular flange 48 (shown in FIG. 1) helps retain a reservoir in the distal end 42 of the handpiece.

The handpiece includes an electromechanical drive mechanism, and is connected to a remote power supply and control via cable 50, which is preferably of suitable operating room quality.

FIG. 3 illustrates an exemplary battery operated handpiece 60 of the present invention, which also contains operator controls and an electromechanical drive mechanism. The operator can control operation of a plunger in a reservoir attached thereto via finger-operated control 62.

Figure 4:
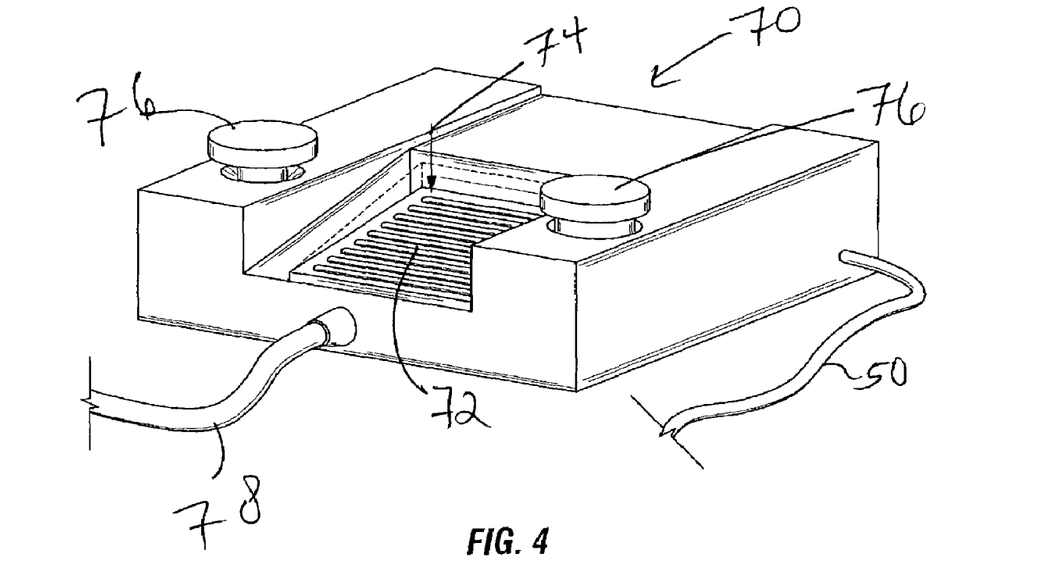
FIG. 4 illustrates an exemplary remote power and control unit suitable for operative connection to the handpiece of FIG. 2, including a footpedal for controlling plunger speed and other foot-operable controls.

FIG. 4 illustrates an exemplary remote power and control unit 70 suitable for operative connection to the handpiece of FIG. 2. A footpedal 72 is used for controlling plunger speed by varying the level of depression shown by arrow 74, and other foot-operable controls 76 can be used to control the direction of plunger travel, actuate the device, or the sensitivity of the footpedal (i.e., maximum and minimum plunger travel speeds). Unit 70 has a power cord 78 of suitable construction for operating room use, and may include a battery backup, including a warning device for indicating low power or when battery power is being used. Appropriate visual displays and audible outputs are provided as one of skill in the art would desire and ordinarily provide for an infusion or aspiration device. A variety of specific circuits and controls for operating the plunger are envisioned and well within the skill of one of ordinary skill in the art; same can be modeled after the Photogenesis "direct drive" delivery systems described in some of the aforementioned patents.

Figure 5:
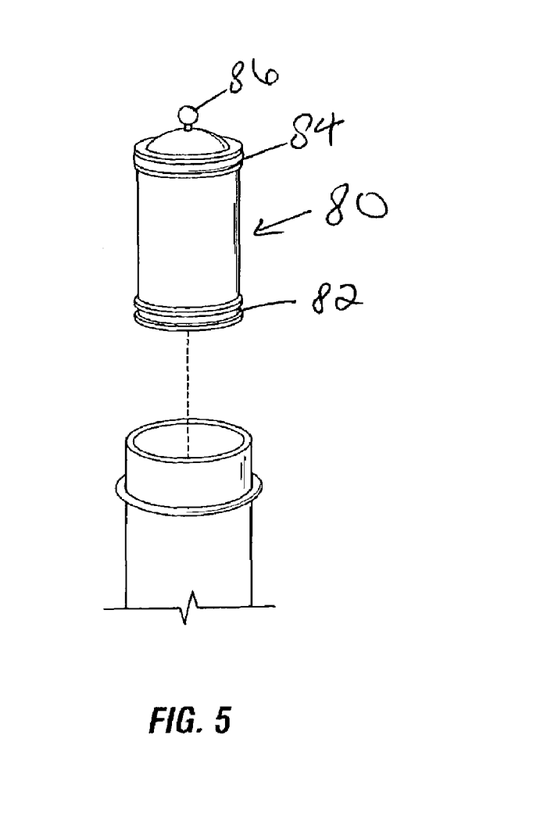
FIG. 5 illustrates an exemplary plunger of the present invention in perspective view with the plunger opening of a reservoir of the present invention.

FIG. 5 illustrates an exemplary plunger 80 of the present invention in perspective view with the plunger opening of a reservoir of the present invention. The plunger is preferably made of stainless steel and corresponds in diameter to the inner diameter of a corresponding reservoir plunger opening and travel channel. One or more grooves 82 are provided, in which a suitable resilient and lubricious O-ring 84 may be attached. A ball 86 is provided at the proximal end of the plunger for detachable attachment to corresponding fitting on a piston 90. The piston is driven by a motor with appropriate gearing. The plungers may be of varying length and diameter depending on the reservoir and application.

Figure 6A:
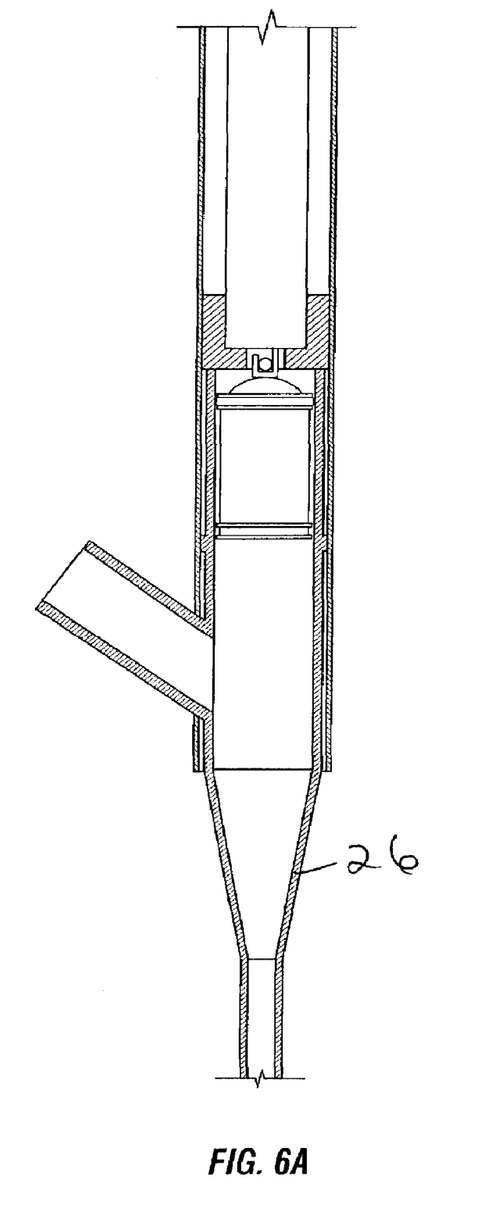
FIGS. 6A and 6B illustrates the plunger of FIG. 5 connected to the handpiece of FIG. 2 or 3 in fully retracted and extended positions, respectively, inside of a reservoir operatively connected to the handpiece.
Figure 6B:
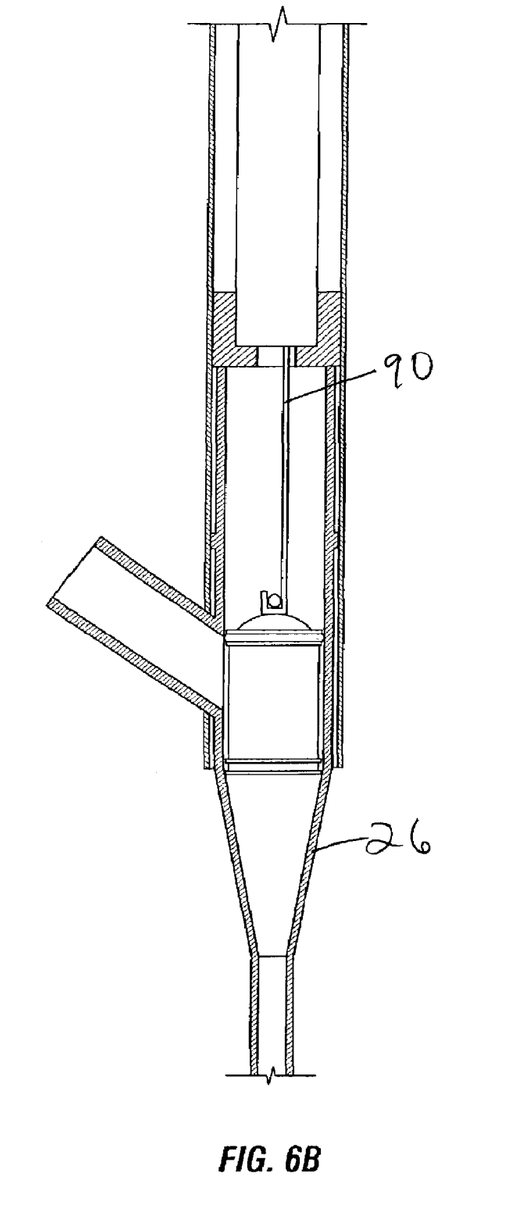

FIGS. 6A and 6B illustrates the plunger of FIG. 5 connected to the handpiece of FIG. 2 or 3 in fully retracted and extended positions, respectively, inside of a reservoir operatively connected to the handpiece. The length and shape of funnel shaped portion 26 may be varied depending on the use, and portion 26 may even be eliminated, for instance when fluids or viscous fluids or being injected.

Figure 7:
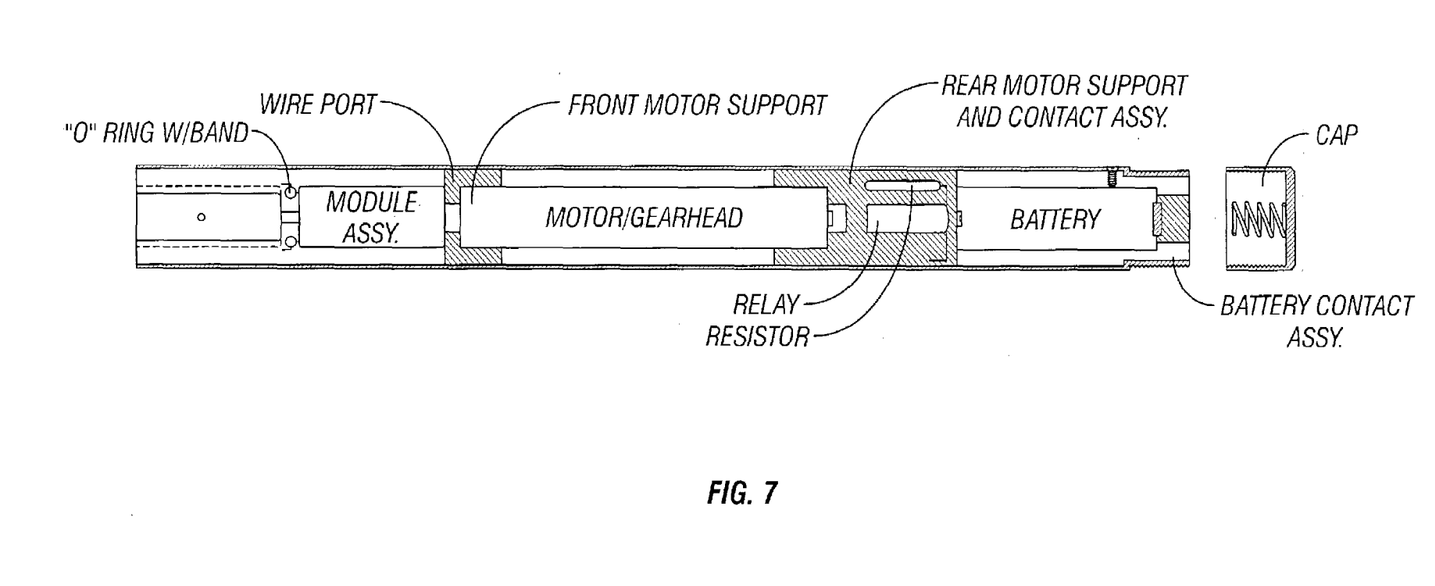
FIG. 7 is a schematic plan view of a battery powered, handpiece such as that illustrated in FIG. 2, including controls and a plunger drive assembly.
Figure 8:
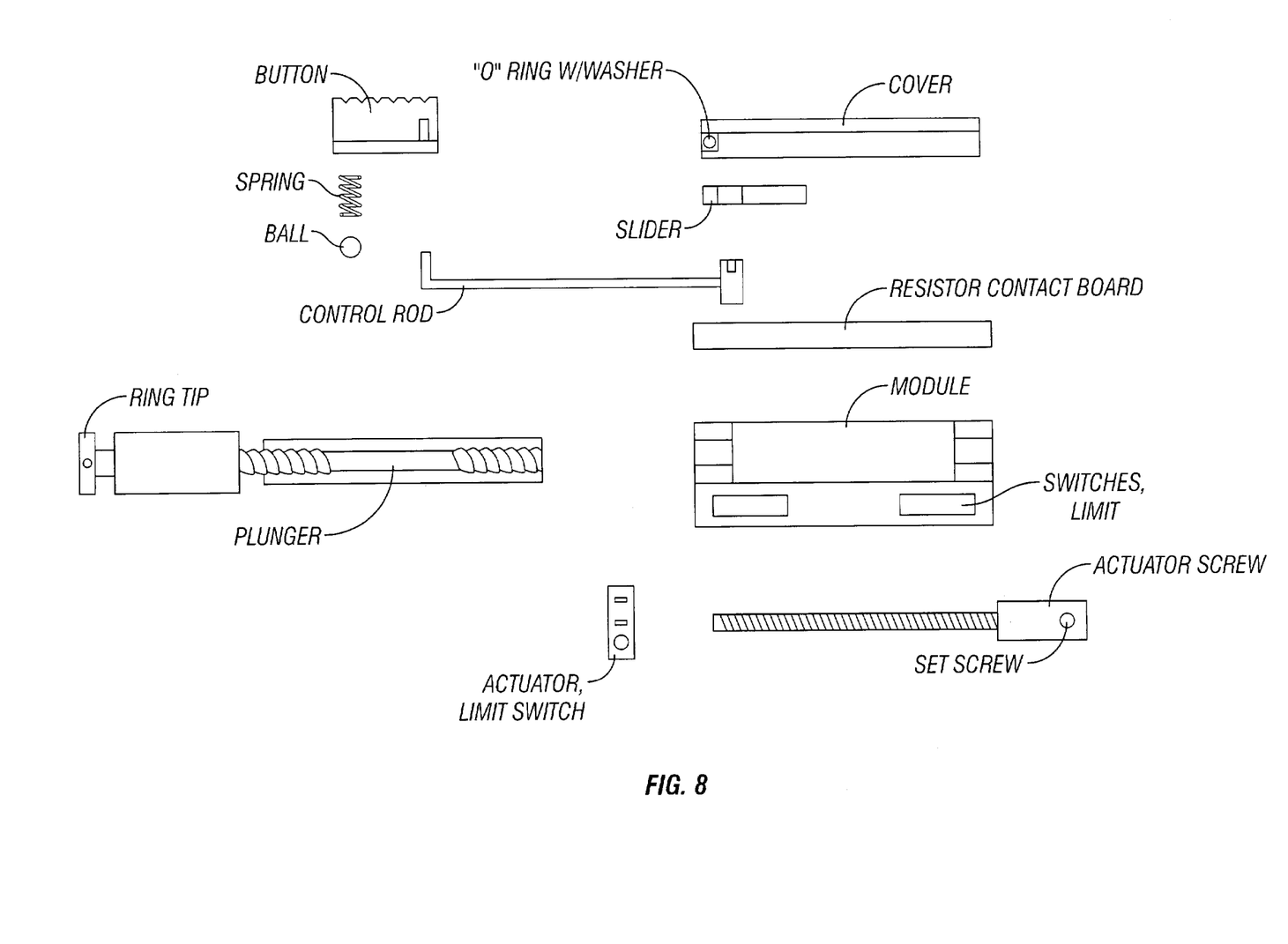
FIGS. 8–45 are exemplary components for use in constructing the exemplary handpiece control of FIG. 3.
Figure 9:
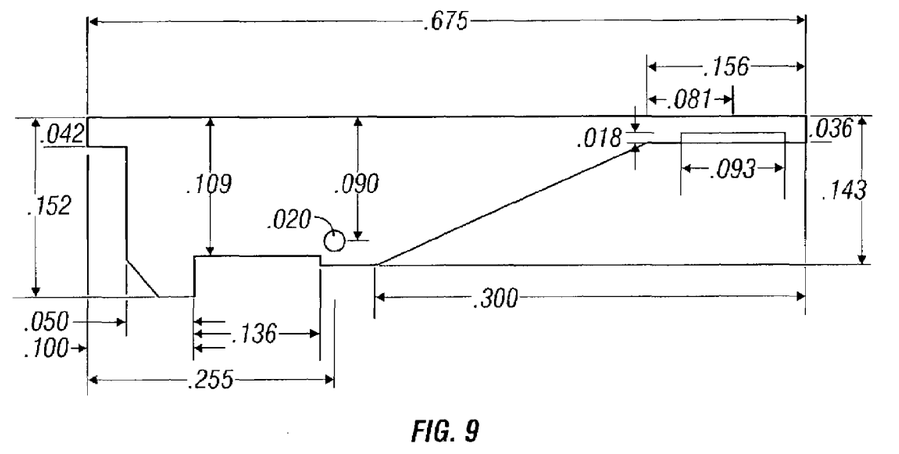
Figure 10:
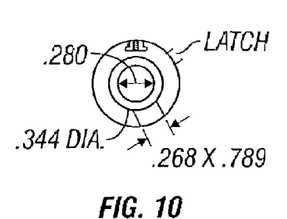
Figure 11:
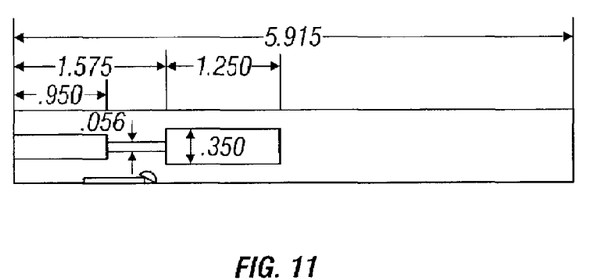
Figure 12:
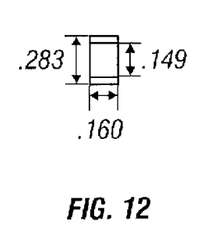
Figure 13:
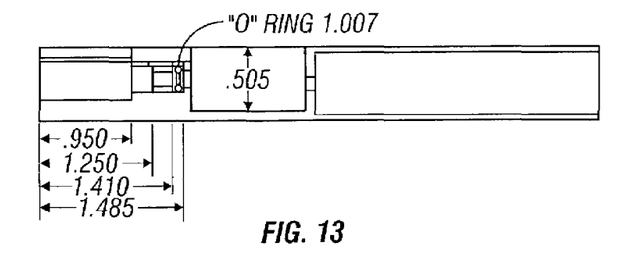
Figure 14:
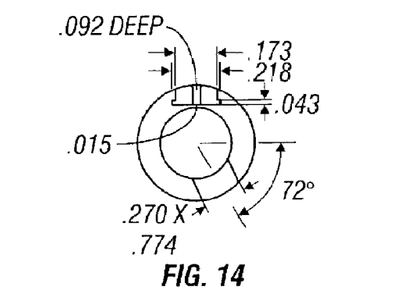
Figure 15:
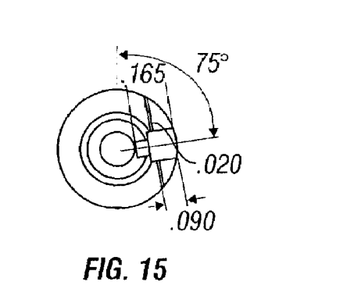
Figure 16:
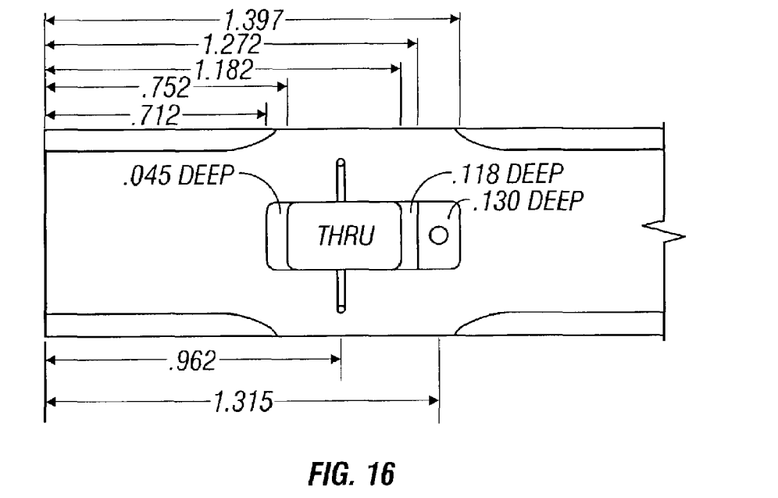
Figure 17:
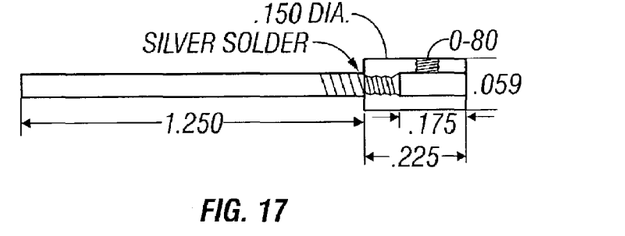
Figure 18:
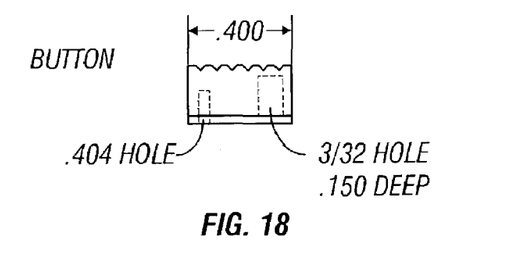
Figure 19:
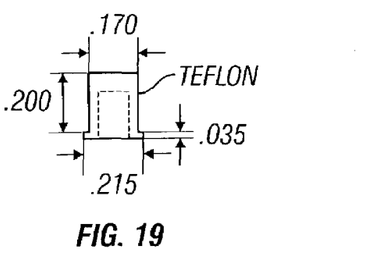
Figure 20:
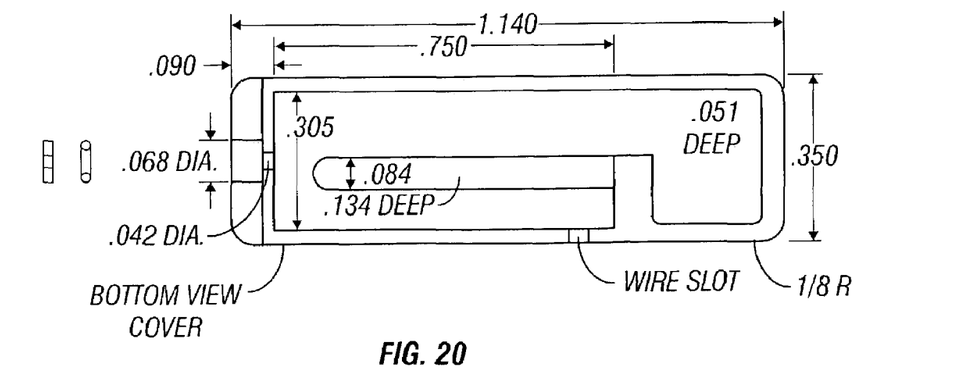
Figure 21:
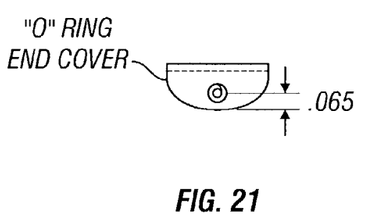
Figure 22:
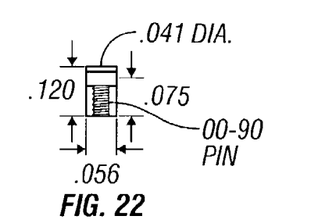
Figure 23:
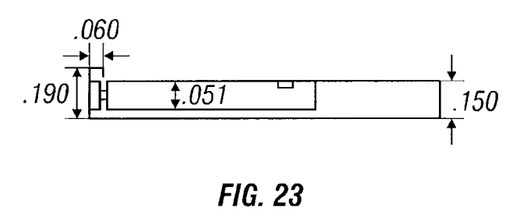
Figure 24:
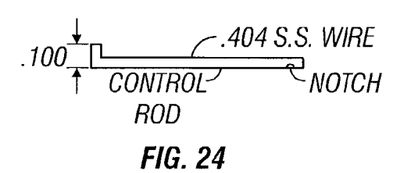
Figure 25:
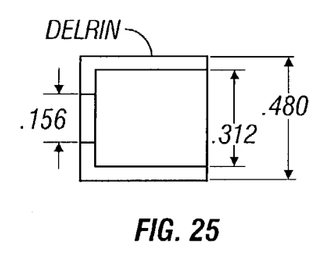
Figures 26, 27:
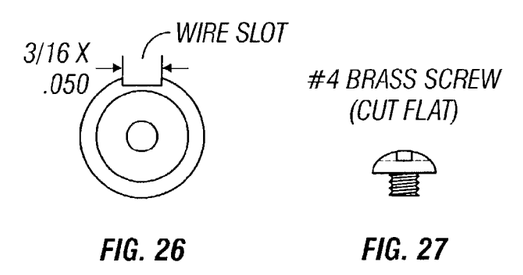
Figure 28:
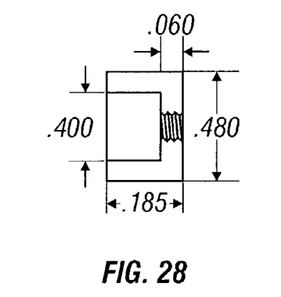
Figure 29:
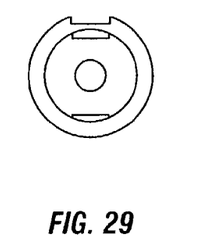
Figure 30:
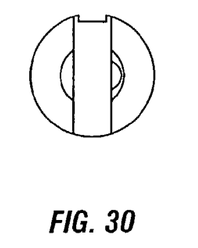
Figure 31:
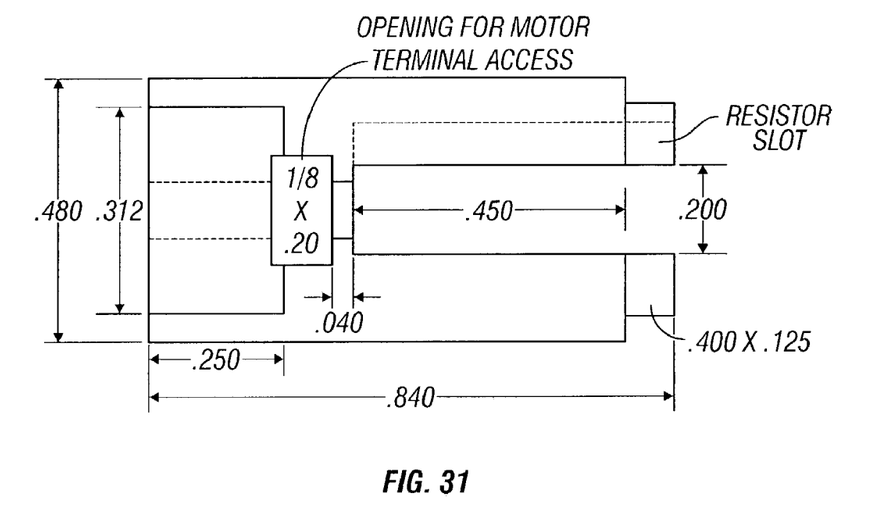
Figure 32:
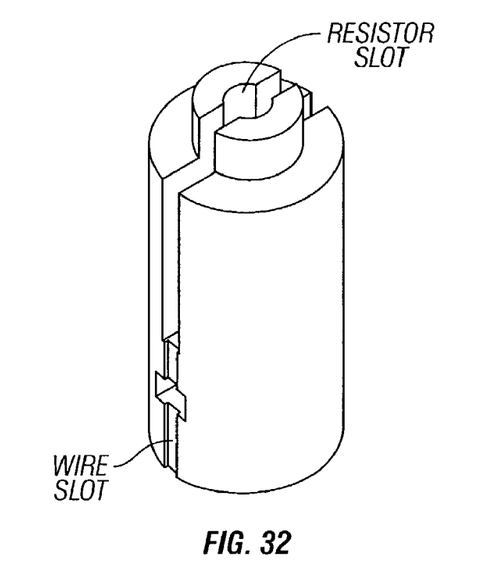
Figure 33:
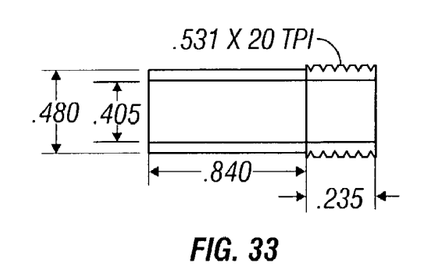
Figure 34:
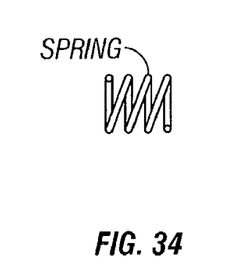
Figure 35:
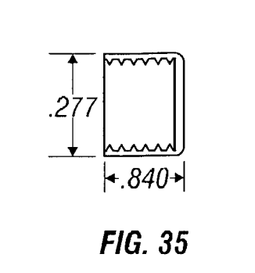
Figure 36:
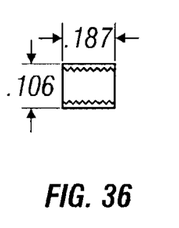
Figure 37:
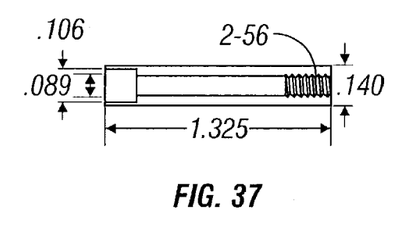
Figure 38:
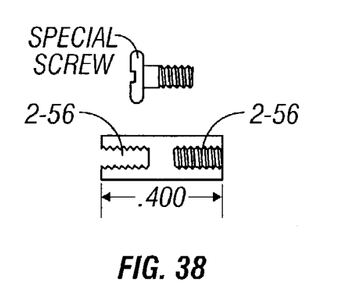
Figure 39:
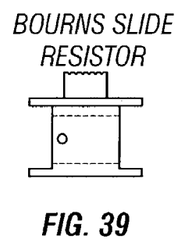
Figure 40:
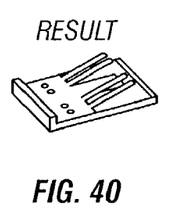
Figure 41:
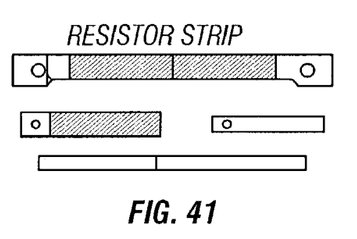
Figure 42:
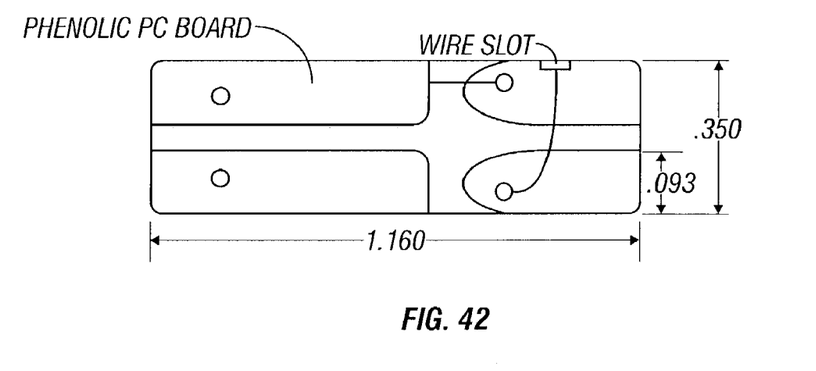
Figure 43:
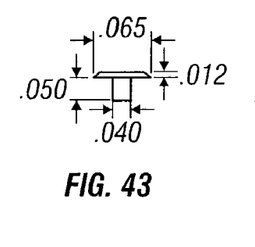
Figure 44:
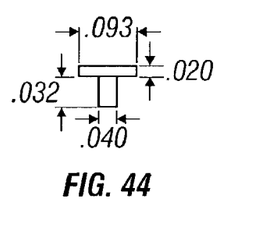
Figure 45:
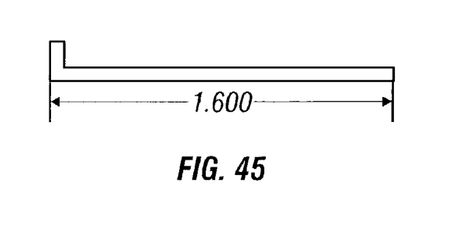

FIG. 7 is a schematic plan view of a battery powered, handpiece such as that illustrated in FIG. 2, including controls and a plunger drive assembly.

FIGS. 8–45 are exemplary components for use in constructing the exemplary handpiece control of FIG. 2. These components, with dimensions as indicated are included in just one of many possible contructions.

The device is preferably used by attaching a plunger to the piston of a handpiece, and slipping the plunger opening of a tip over the plunger. The locking ring 46 is then rotated to block release of the tip from the handpiece, and the carrier fluid and implant placed into the loading channel ("sidearm").

The device as disclosed herein has been successfully used to safely implant retinal cell grafts, such as photoreceptor and RPE cells prepared as described in the aforementioned patents, into the subretinal space of human patients suffering from retinitis pigmentosa and AMD, and may be used to also treat other diseases. The carrier solution may include various drugs and other medicaments to treat patients.

Preferred tip dimensions as illustrated by part numbers in FIG. 6A, include a top portion 100 that is 12 mm in length, a main reservoir portion 102 that is 17 mm in length, have a inner diameter of 4.8 mm at the plunger opening, and is transparent. The sidearm may have a 5 mm inner diameter. Preferably, Cannula 28 can have an inner diameter (ID) of 0.7 mm or 0.5 mm, and outer diameter of 0.8 mm or 0.6 mm respectively. The plastic components can be formed of suitable medical grade plastic and injection molded. The non-plastic part can be fused to the plastic parts by standard techniques known to those of ordinary skill in the art.

It is to be understood that the invention may be practiced other than as specifically described herein, wherein the scope of protection requested is defined by the following claims with the foregoing being utilized to describe exemplary and preferred embodiments only.

I claim:

1. An implantation device for implanting a solid or semisolid implant into a mammal or human, comprising:
   a reservoir for holding an implant and a carrier fluid, wherein said reservoir includes a cannula, said cannula having a tip end and a delivery opening therein both shaped and dimensioned so said device can implant an implant into the subretinal space of a mammalian or human eye, wherein an implant and carrier fluid can be expressed from said delivery opening into the subretinal space of the recipient eye, wherein the cannula is of sufficient length that the tip end can reach the subretinal space while the remainder of the fluid reservoir is external of the eye, wherein said tip end is bent to accommodate the shape of the back of the eye, wherein expression of the carrier fluid from the reservoir via said delivery opening expels the implant through said delivery opening.

2. The device of claim 1, wherein said reservoir further comprises a plunger opening and a plunger travel channel, wherein a plunger may be inserted through said plunger opening into said plunger travel channel to express fluid in said reservoir.

3. The device of claim 2, further comprising a plunger at least partially slidably disposed in said plunger travel channel.

4. The device of claim 2, wherein said reservoir further comprises a loading channel and a loading channel opening, wherein said loading channel may be accessed via said loading channel opening independently of said plunger opening.

5. The device of claim 3, wherein said reservoir further comprises a loading channel and a loading channel opening, wherein said loading channel may be accessed via said loading channel opening independently of said plunger opening.

6. The device of claim 5, wherein said loading channel is operatively connected to said plunger travel channel at a junction point, wherein said plunger may slidably travel through said plunger travel channel towards said cannula sufficiently past said junction point to block fluid flow from said plunger travel into said loading channel.

7. The device of claim 3, further comprising a handpiece that is operatively connectable to said reservoir, wherein said handpiece comprises an electromechanical drive apparatus, wherein said plunger is drivable by said electromechanical drive apparatus.

8. The device of claim 7, wherein said drive apparatus further comprises operator controls for controlling forward and reverse motion of said plunger in said plunger travel channel.

9. The device of claim 7, further comprising a control unit remotely connected to said drive apparatus, wherein said control unit comprises operator controls and a power supply far said drive apparatus.

10. The device of claim 9, wherein said operator controls comprise a footpedal for operating said controls.

11. The device of claim 1, further comprising a retinal cell graft.

12. The device of claim 6, further comprising a retinal cell graft.

13. The device of claim 7, wherein said plunger is connectable and disconnectable to said electromechanical drive apparatus by a user at the site of use.

14. An implantation device for implanting a solid or semisolid implant into a mammal or human eye, comprising:
a reservoir for holding an implant and a carrier fluid, said reservoir holding an implant comprising a retinal cell graft, wherein said reservoir includes a cannula, said cannula having a tip end and a delivery opening therein both shaped and dimensioned so said device can implant said implant into the subretinal space of a mammalian or human eye, wherein said implant and carrier fluid can be expressed from said delivery opening into the subretinal space of the recipient eye, wherein the cannula is of sufficient length that the tip end can reach the subretinal space while the remainder of the fluid reservoir is external of the eye, wherein expression of the carrier fluid from the reservoir via said delivery opening expels said implant through said delivery opening.

15. The device of claim 1, wherein said reservoir further comprises a plunger opening, a plunger travel channel, and a plunger at least partially slidably disposed in said plunger travel channel, wherein said plunger may be inserted through said plunger opening into said plunger travel channel to express fluid in said reservoir.

16. The device of claim 15, wherein said reservoir further comprises a loading channel and a loading channel opening, wherein said loading channel may be accessed via said loading channel opening independently of said plunger opening.

17. The device of claim 16, wherein said reservoir further comprises a loading channel and a loading channel opening, wherein said loading channel may be accessed via said loading channel opening independently of said plunger opening, wherein said loading channel is operatively connected to said plunger travel channel at a junction point, wherein said plunger may slidably travel through said plunger travel channel towards said cannula sufficiently past said junction point to block fluid flow from said plunger travel into said loading channel.

18. The device of claim 15, further comprising a handpiece that is operatively connectable to said reservoir, wherein said handpiece comprises an electromechanical drive apparatus, wherein said plunger is drivable by said electromechanical drive apparatus.

19. The device of claim 18, wherein said drive apparatus further comprises operator controls for controlling forward and reverse motion of said plunger in said plunger travel channel, and a control unit remotely connected to said drive apparatus, wherein said control unit comprises operator controls and a power supply for said drive apparatus.

20. The device of claim 19, wherein said operator controls comprise a footpedal for operating said controls.

* * * * *